United States Patent
Kobayashi et al.

(10) Patent No.: US 7,495,358 B2
(45) Date of Patent: Feb. 24, 2009

(54) VIBRATORY LINEAR ACTUATOR AND ELECTRIC TOOTHBRUSH USING THE SAME

(75) Inventors: Noboru Kobayashi, Omihachiman (JP); Takahiro Nishinaka, Omihachiman (JP); Kensaku Kanada, Hikone (JP); Hiroaki Shimizu, Hikone (JP); Ryo Motohashi, Hikone (JP); Hidekazu Yabuuchi, Hikone (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 469 days.

(21) Appl. No.: 11/330,202

(22) Filed: Jan. 12, 2006

(65) Prior Publication Data

US 2006/0158048 A1   Jul. 20, 2006

(30) Foreign Application Priority Data

Jan. 19, 2005   (JP) ............................. 2005-012084

(51) Int. Cl.
 *H02K 33/00*   (2006.01)
(52) U.S. Cl. .............................. 310/36; 310/15; 310/17; 15/22.1; 15/22.2
(58) Field of Classification Search .................. 310/15, 310/17, 36; 15/22.1, 22.2
See application file for complete search history.

(56) References Cited

U.S. PATENT DOCUMENTS

| 5,921,134 A | * | 7/1999 | Shiba et al. .................... 74/110 |
| 6,991,217 B2 | * | 1/2006 | Shimizu et al. ............. 251/284 |
| 2002/0154188 A1 | * | 10/2002 | Hiyane et al. ................. 347/37 |
| 2002/0195884 A1 | | 12/2002 | Ichii et al. |
| 2004/0010871 A1 | | 1/2004 | Nishinaka et al. |

FOREIGN PATENT DOCUMENTS

| EP | 1193844 | 4/2002 |
| EP | 1329203 | 7/2003 |
| JP | 2001-314070 | 11/2001 |
| JP | 2002-176758 | 6/2002 |
| JP | 3475949 | 9/2003 |
| JP | 2004-343933 | 12/2004 |

OTHER PUBLICATIONS

U.S. Appl. No. 10/557,253 to Shimizu et al., filed Nov. 16, 2005.
U.S. Appl. No. 10/557,055 to Shimizu et al., filed Nov. 16, 2005.

(Continued)

*Primary Examiner*—Gary F. Paumen
(74) *Attorney, Agent, or Firm*—Greenblum & Bernstein, P.L.C.

(57) ABSTRACT

A vibratory linear actuator according to one embodiment of the present invention is comprised of a stator having a through hole therein and a winding wire therearound, a movable member having a through hole therein and a member made of a magnetic material, said movable member being provided inside said through hole of said stator, so as to reciprocate in an axis direction upon an application of electric current to said winding wire, a shaft inserted into said through hole of said movable member so as to be movable reciprocally in relation to said movable member, and a coordinating member that enables said shaft to reciprocate in opposite phase to said movable member.

20 Claims, 5 Drawing Sheets

OTHER PUBLICATIONS

U.S. Appl. No. 10/557,252 to Shimizu et al., filed Nov. 16, 2005.
U.S. Appl. No. 11/330,204 to Shimizu et al., filed Jan. 12, 2006.
English language Abstract of JP 2002-176758.
An English language abstract of patent family member Japanese Laid-open Patent Publication No. 2002-199689.
English language Abstract of JP 2004-343933.
English language Abstract of JP 2001-314070.

* cited by examiner

VIBRATORY LINEAR ACTUATOR AND ELECTRIC TOOTHBRUSH USING THE SAME

CROSS REFERENCE TO RELATED APPLICATION

This application claims benefit of priority under 35 U.S.C. § 119 to Japanese Patent Application No. 2005-12084, filed on Jan. 19, 2005, the entire contents of which are incorporated by reference herein.

BACKGROUND OF THE INVENTION

1. Field of the Invention

The present invention relates to a vibratory linear actuator and an electric toothbrush using the same.

2. Description of the Related Art

One example of a vibratory linear actuator, specifically for preferable use as a driving source of an electric toothbrush has been known as composed of a cylindrical stator having a winding wire, a cylindrical movable element that is provided with a member made of a magnetic material and disposed inside the stator, and a shaft attached on the movable member (See Japanese Patent Application Laid-open Publication No. 2002-176758).

In addition, there has been known another vibratory linear actuator that is provided with a vibration absorbing weight moving independently from the movable member to reduce or offset unwanted vibration in order to eliminate a disadvantage of vibration caused by inertial force of the movable member (See Japanese Patent Publication No. 3475949).

However, when the vibration absorbing weight moving in opposite phase to the movable member is used to reduce vibration, the vibratory linear actuator inevitably becomes larger in size. In addition, since the use of the vibration absorbing weight leads to an increased weight of moving components including the movable member and the weight, more energy is required to reciprocate the components.

Therefore, an electric toothbrush using such a vibratory linear actuator also has disadvantages in terms of downsizing and energy saving.

SUMMARY OF THE INVENTION

The present invention has been made in view of the above disadvantage and the objective thereof is a provision of a compact and efficient vibratory linear actuator and an electric toothbrush using the same.

In order to achieve the above objective, a vibratory linear actuator comprising a stator having a through hole therein and a winding wire therearound; a movable member having a through hole therein and a member made of a magnetic material, the movable member being provided inside the through hole of the stator, so as to reciprocate in an axis direction upon an application of electric current to the winding wire; a shaft inserted into the through hole of the movable member so as to be movable reciprocally in relation to the movable member; and a coordinating member that enables the shaft to reciprocate in opposite phase to the movable member.

In the vibratory linear actuator, the shaft serves as a vibration absorbing member for offsetting or reducing vibration caused by inertia of the movable member.

In this case, when the above movable member is supported by the bearing provided between the shaft and the movable member, it is advantageous to reduce the outer diameter of the vibratory linear actuator as a whole. On the other hand, when the movable member is supported by the bearing provided between the stator and the movable member, the magnetic gap between the stator and the movable member is maintained constant without being affected by deflection of the shaft or the like, thereby producing higher magnetic driving force.

In addition, when the above bearing is composed of the rolling element and the support member that supports the rolling element and is made of a nonmagnetic material, the rolling element which is even made of a magnetic material is not directly attracted by the magnetic force produced by a magnetic circuit, thereby reducing the driving loss.

When the above bearing is composed of the rolling element made of a nonmagnetic material and the support member that supports the rolling element, the rolling element is not directly attracted by the magnetic force produced by the magnetic circuit, thereby reducing the driving loss.

As the above coordinating member, the spring member connecting the movable member and the shaft is preferably employed. In this case, the movable member and the shaft constitute a spring oscillation system, thereby facilitating to output higher power.

As the coordinating member, the link member connecting the movable member and the shaft can be employed, thereby ensuring linear reciprocating movement of the shaft.

The electric toothbrush according to the present invention is characterized in that it comprises the above vibratory linear actuator as a driving source and the brush for brushing teeth, thereby providing a compact, lightweight, and low-vibration electric toothbrush.

According to the present invention, the shaft serves as the vibration absorbing member by being linearly reciprocated in opposite phase to the movable member by magnetic force. Since an additional vibration absorbing weight is unnecessary to reduce unwanted vibration, thereby providing advantages in terms of downsizing and weight saving. In addition, since a large amount of driving energy is not necessary, the vibratory linear actuator is further advantageous in terms of downsizing.

DESCRIPTION OF THE PREFERRED EMBODIMENTS

Figure 1:
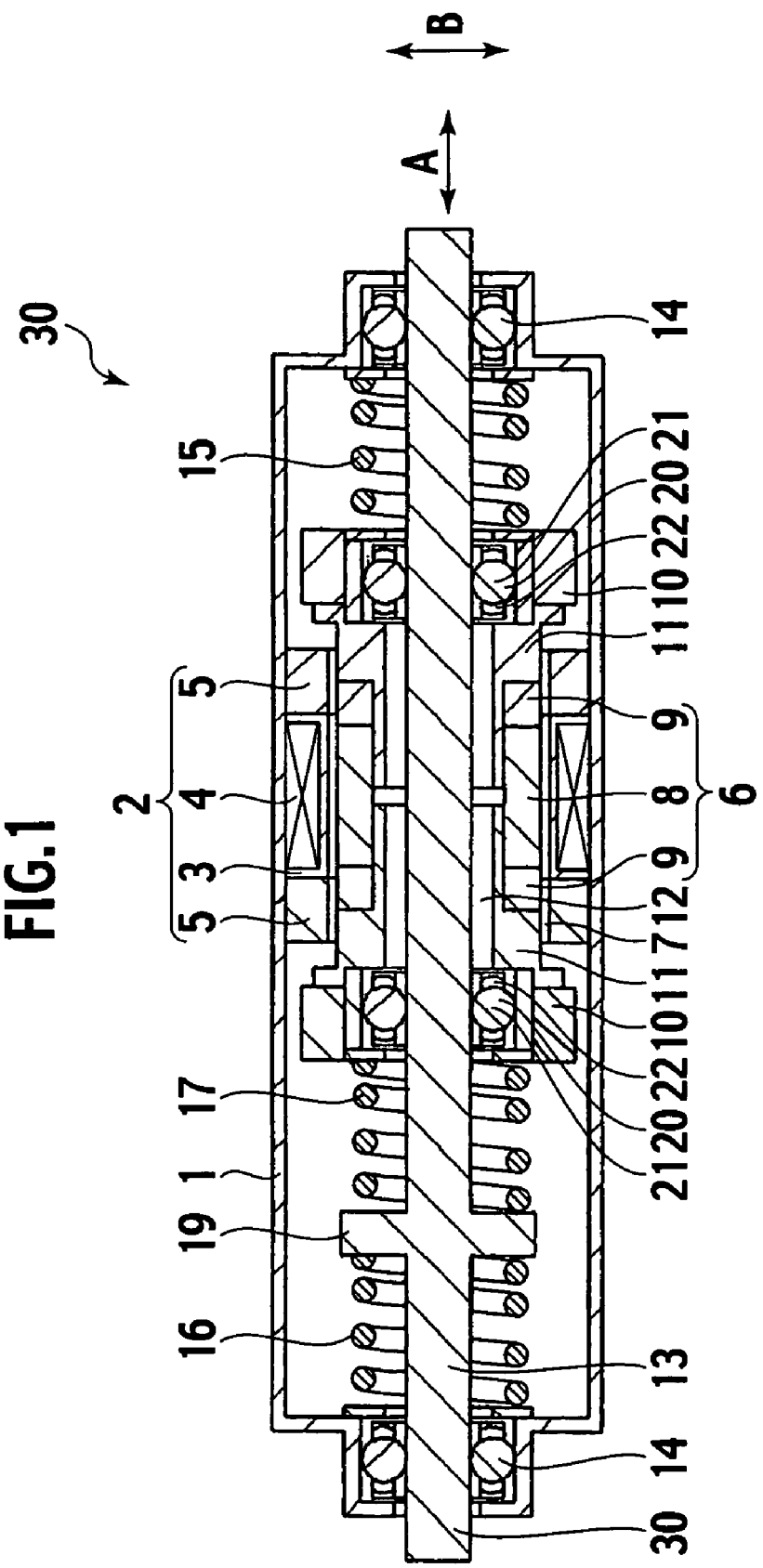
FIG. 1 is a cross-sectional view of a vibratory linear actuator according to one embodiment of the present invention.
Figure 2:
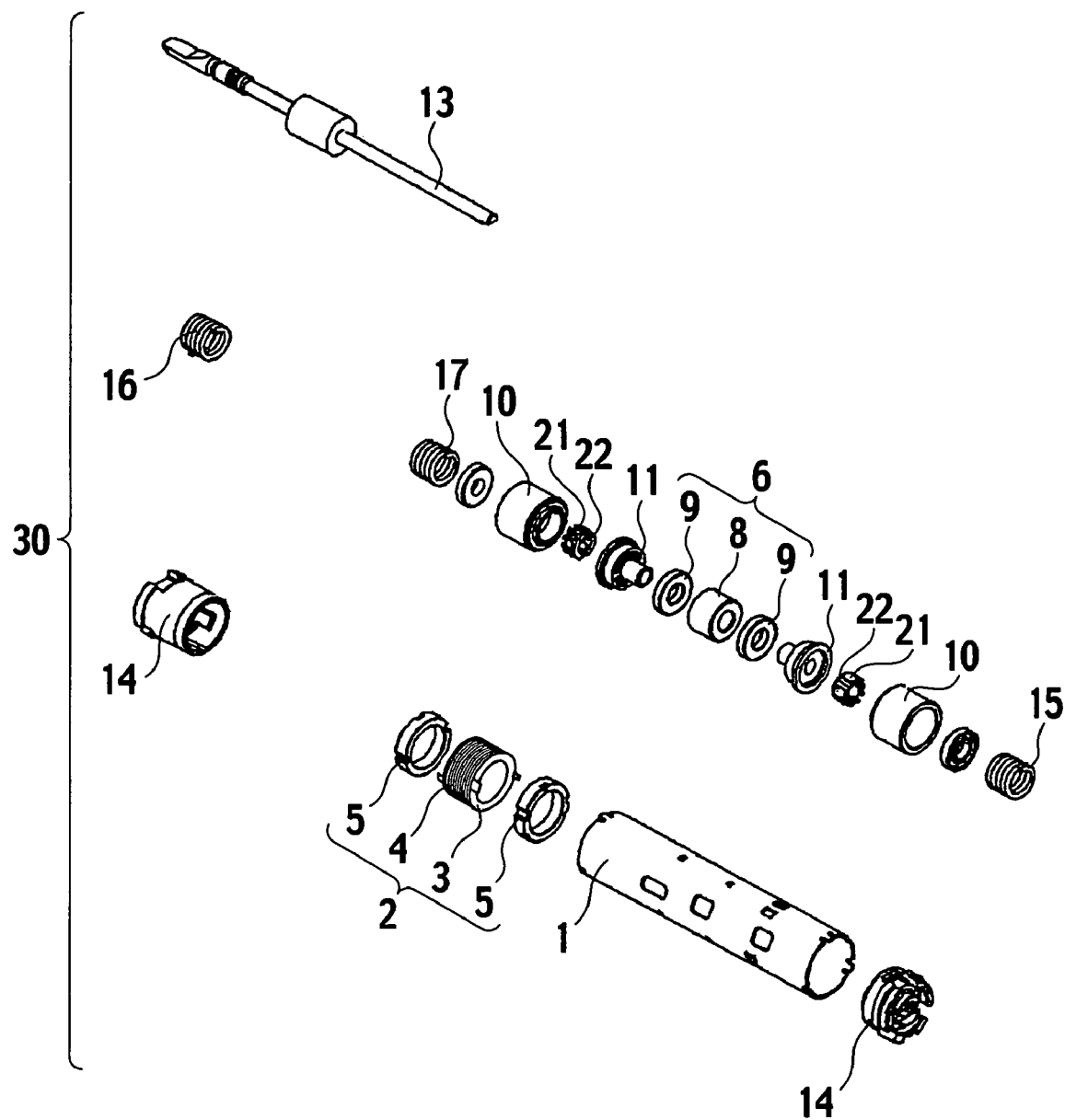
FIG. 2 is an exploded perspective view of the vibratory linear actuator illustrated in FIG. 1.

Referring to accompanying drawings, preferred embodiments of the present invention will be described in detail. FIGS. 1 and 2 are a cross-sectional view and an exploded perspective view of a vibratory linear actuator 30 according to one embodiment of the present invention, respectively. As illustrated, a cylindrical stator 2 is provided inside a cylindrical shield case 1 and a shaft 13 is attached by bearings 14, 14 so as to be able to reciprocate linearly along an axis direction A. The stator 2 is composed of a coil member made by winding wire 4 (a winding wire 4, hereinafter) around a coil bobbin 3 and cylindrical stationary parts 5,5 provided on both sides of the coil bobbin 3.

Inside the stator 2 is provided a cylindrical movable member 6. Specifically, the movable member 6 is supported by bearings 20, 20 fitted on the shaft 13 in such a way that a predetermined magnetic gap 7 is maintained between the outer surface of the movable member 6 and the inner surface of the stator 2. The movable member 6 is composed of a cylindrical yoke 8 made of a magnetic material and cylindrical permanent magnets 9, 9 provided on both sides of the yoke 8 in the axis direction A. The permanent magnets 9, 9 are positioned so that the circumference thereof faces the inner surface of the stationary parts 5. In addition, each of the permanent magnets 9, 9 has different magnetic poles on each side. Also, the outer surface of one of the permanent magnets 9, 9 has the same magnetic pole as the outer surface of the other of the permanent magnets 9, 9, wherein the outer surface is a surface of the permanent magnets 9, 9 that does not meets the yoke 8. Furthermore, next to the outer surfaces of the permanent magnets 9, 9 are disposed the bearings 20, 20 and weight adjusting weights 10, 10 with a connection member 11 between the permanent magnet 9 and the bearing 20. By the way, although the movable member 6 including the permanent magnets 9, 9 is exemplified here, the movable member 6 may have an alternative member made of a magnetic material instead of the permanent magnets 9, 9.

The shaft 13 is inserted into a through hole 12 penetrating the cylindrical movable member 6. It should be noted that the movable member 6 is movable along the axis direction A by means of the bearings 20, 20. Between one end of the movable member 6 and one end (the right end in FIG. 1) of the shield case 1 is disposed a spring member 15 made of a coil spring; between the other end of the movable member 6 and a spring support member 19 attached on the shaft 13 is disposed a spring member 17 made of a coil spring; and between the spring support member 19 and the other end of the shield case 1 is disposed a spring member 16 made of a coil spring.

These spring members 15, 16, 17 constitute a spring oscillation system along with the movable member 6 and the shaft 13 and serve as a coordinating member that enables the shaft 13 to reciprocate in opposite phase to the movable member 6. Namely, when the movable member 6 is driven reciprocally by a magnetic circuit created by the winding wire 4 of the stator 2 and the permanent magnets 9, 9 of the movable member 6, the shaft 13 is able to reciprocally move in opposite phase to the movable member 6 under resonance condition by substantially matching a frequency of the alternating current applied to the winding wire 4 with a resonance frequency determined in accordance with a spring constant of the spring members 15, 16, 17 and a total mass of the movable member 6 and the shaft 13, both of which belong to the spring oscillation system.

Since the shaft 13 and the movable member 6 offset the unwanted vibration caused by each other, there is no need to provide a separate vibration absorbing weight. In addition, since the shaft 13 is inserted into the through hole 12 of the movable member 6, the vibratory linear actuator 30 is downsized while reducing unwanted vibration. Furthermore, since it is possible to reduce the mass of the moving portion as a whole, the vibratory linear actuator 30 becomes highly efficient.

Figure 3:
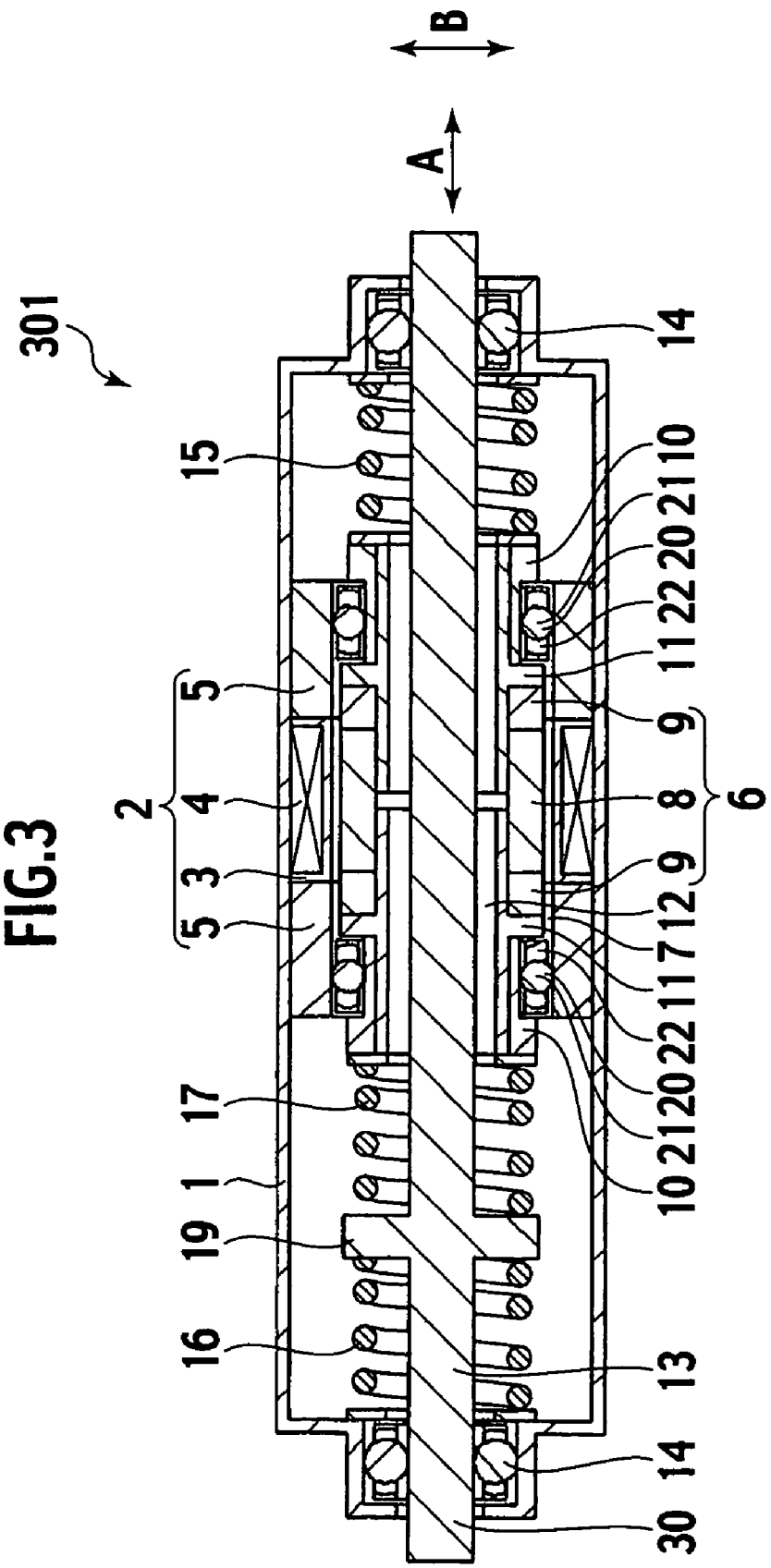
FIG. 3 is a cross-sectional view of a vibratory linear actuator according to another embodiment of the present invention.

Although the bearings 20, 20 for supporting the shaft 13 are disposed away from the inside of the stator 2 so as to downsize the vibratory linear actuator 30 in the radial direction B in this embodiment, the bearings 20, 20 can be disposed between the inner surface of the stator 2 and the outer surface of the movable member 6, as in a vibratory linear actuator 301 illustrated in FIG. 3. In this case, the magnetic gap 7 between the movable member 6 and the stator 2 is maintained constant without being affected by deflection of the shaft 2 or the like, thereby obtaining stable magnetic force. Additionally, the bearing 20 may be disposed between the movable member 6 and the shield case 1 on which the stator 2 is secured.

By the way, when the bearings 20, 20 are composed of a rolling element 21 (a ball 21 in FIGS. 1, 3, and 4) and a supporting member 22 for supporting the rolling member 21, either one of the rolling element 21 and the supporting member 22 is preferably made of a nonmagnetic material. Because of this, the rolling element 21 is not affected by the magnetic force exerted by the magnetic circuit, thereby reducing driving loss.

Figure 4:
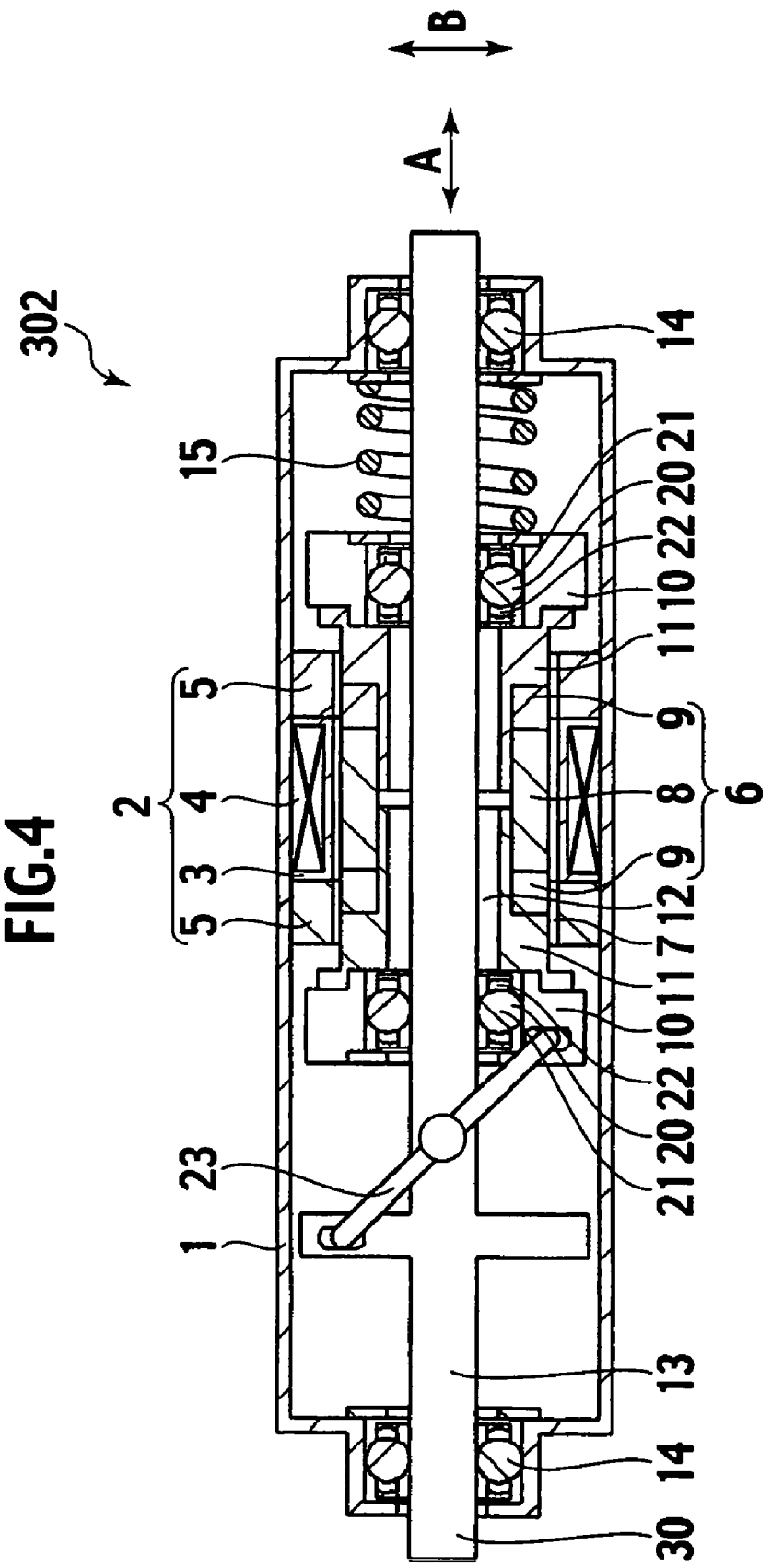
FIG. 4 is a cross-sectional view of a vibratory linear actuator according to yet another embodiment of the present invention.

FIG. 4 illustrates a vibratory linear actuator 302 according to another embodiment. In this embodiment, a coordinating member for moving the shaft 13 in opposite phase to the movable member 2 is composed of a link member 23. One end of the link member 23 is connected to the movable member 6; the other end of the link member 23 is connected to the shaft 13; and a middle portion of the link member 23 is supported by the shield case 1. When the movable member 6 reciprocates, the shaft 13 is able to reciprocate in opposite phase to the movable member 6 irrespective of the vibration frequency.

Although the stator 2, the movable member 6, and the shaft 13 have a shape of a cylinder in the above embodiments, they are not necessarily formed into this shape. For example, they can be fabricated into a shape of a polygonal pole. It is needless to say even in this case that the stator 2 has to have a through hole (or hollow space) to have the movable member 6 therein and similarly the movable member 6 has to have a through hole into which the shaft 13 is inserted.

Figure 5:
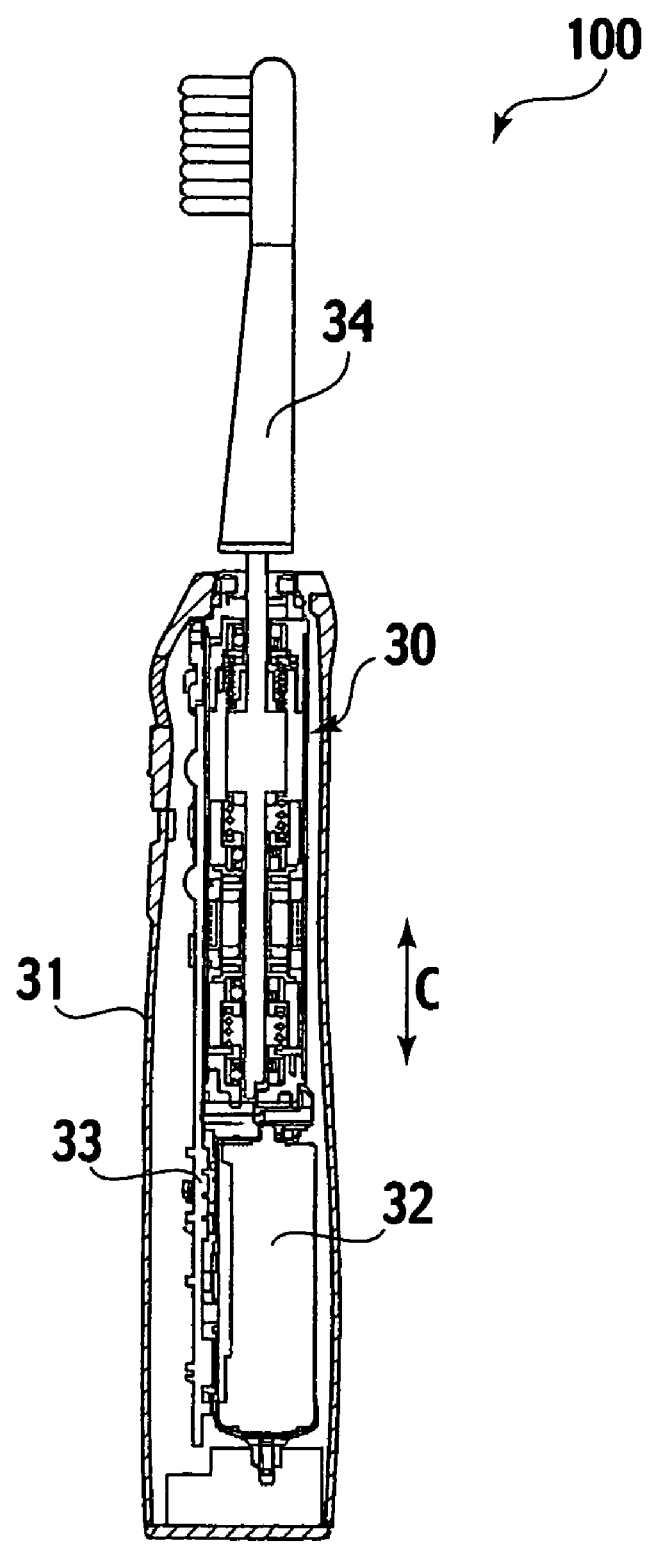
FIG. 5 is a cross-sectional view of an electric toothbrush according to one embodiment of the present invention.

The vibratory linear actuator according to the present invention can be employed as various kinds of driving source, one example of which is illustrated in FIG. 5 as an electric toothbrush. As illustrated, an electric toothbrush 100 includes a housing 31, a vibratory linear actuator 30 which is constructed per the foregoing embodiments, a battery 32 as a power source, a control circuit 33 for providing alternating current to the winding wire 4 of the vibratory linear actuator 30, and a brush 34 for brushing teeth. The vibratory linear actuator 30 and the battery 32 are disposed side by side along a longitudinal direction C inside the housing 31. The brush 34 is attached on the distal end of the shaft 13 protruding in the longitudinal direction C from the housing 31 and driven reciprocally by the shaft 13. The electric toothbrush 100 provides a comfortable use for its users because the vibratory linear actuator as a driving source is not only compact but also capable of reducing unwanted vibration and producing higher output power due to its reduced weight.

By the way, although the electric toothbrush 100 is comprised of the vibratory linear actuator 30, it is apparently understood that an electric toothbrush according to the present invention may comprise the aforementioned vibratory linear actuators 300, 301.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A vibratory linear actuator comprising:
   a stator having a through hole therein and a winding wire therearound,
   a movable member having a through hole therein and a member made of a magnetic material, said movable member being provided inside said through hole of said stator, so as to reciprocate in an axis direction upon an application of electric current to said winding wire,
   a shaft inserted into said through hole of said movable member so as to be movable reciprocally in relation to said movable member, and
   a coordinating member that enables said shaft to reciprocate in opposite phase to said movable member.

2. A vibratory linear actuator as recited in claim 1, wherein said movable member is supported by a bearing member disposed between said shaft and said movable member.

3. A vibratory linear actuator as recited in claim 1, wherein said movable member is supported by a bearing member disposed between said stator and said movable member.

4. A vibratory linear actuator as recited in claim 2, wherein said bearing member includes a rolling element and a support member made of a nonmagnetic material for supporting said rolling element.

5. A vibratory linear actuator as recited in claim 3, wherein said bearing member includes a rolling element and a support member made of a nonmagnetic material for supporting said rolling element.

6. A vibratory linear actuator as recited in claim 2, wherein said bearing member includes a rolling element made of a nonmagnetic material and a support member for supporting said rolling element.

7. A vibratory linear actuator as recited in claim 3, wherein said bearing member includes a rolling element made of a nonmagnetic material and a support member for supporting said rolling element.

8. A vibratory linear actuator as recited in claim 1, wherein said coordinating member is a spring member connecting said movable member and said shaft.

9. A vibratory linear actuator as recited in claim 1, wherein said coordinating member is a link member connecting said movable member and said shaft.

10. An electric toothbrush comprising a vibratory linear actuator as recited in claim 1 as a driving source and a brush for brushing teeth, said brush being driven by said shaft.

11. The vibratory linear actuator as recited in claim 1, wherein said shaft comprises a nonmagnetic material.

12. The vibratory linear actuator as recited in claim 1, wherein said shaft is supported by said moveable member.

13. The vibratory linear actuator as recited in claim 1, further comprising a housing disposed about said stator, said movable member, said shaft, and said coordinating member.

14. The vibratory linear actuator as recited in claim 13, wherein said housing extends between a pair of housing ends and one of said housing ends defines an aperture and said shaft extends axially along said housing and through said aperture.

15. The vibratory linear actuator as recited in claim 13, wherein said housing extends between a pair of housing ends, said shaft includes a spring support extending radially outward of said shaft, and said coordinating member comprises:
   a first spring extending between said moveable member and one of said housing ends;
   a second spring extending between said moveable member and said spring support; and
   a third spring extending between said spring support and the other of said housing ends.

16. The vibratory linear actuator as recited in claim 15, wherein one of said housing ends defines an aperture and said shaft extends axially along said housing and though said aperture.

17. An electric toothbrush comprising:
   a housing extending between a pair of housing ends;
   at least one of said housing ends defining a housing end aperture;
   a stator defining a hole extending though said stator and including a winding wire wound about said stator, said stator disposed in said housing;
   a movable member defining a hole extending through said movable member and including a member comprising a magnetic material, said movable member disposed in said stator hole for reciprocating axially with respect to said stator in response to application of electric current to said winding wire;
   a shaft disposed in said moveable member hole and extending axially along said housing and through said housing end aperture; and
   a coordinating member disposed in said housing and configured to reciprocate said shaft in opposite phase to a reciprocating phase of said moveable member.

18. The electric toothbrush as set forth in claim 17, wherein said shaft includes a spring support extending radially outwardly of said shaft, said coordinating member comprising:
   a first spring extending between said moveable member and one of said housing ends;
   a second spring extending between said moveable member and said spring support; and
   a third spring extending between said spring support and the other of said housing ends.

19. The electric toothbrush as set forth in claim 17, wherein said shaft includes a link support extending radially outwardly of said shaft, said coordinating member comprising a link member interconnecting said movable member and said link support.

20. The electric toothbrush as set forth in claim 17, wherein a bearing operably interconnects said movable member and said shaft for reciprocally moving said movable member and said shaft in opposite phase to one another.

* * * * *